United States Patent [19]

Gombotz et al.

[11] Patent Number: 5,019,400
[45] Date of Patent: May 28, 1991

[54] VERY LOW TEMPERATURE CASTING OF CONTROLLED RELEASE MICROSPHERES

[75] Inventors: Wayne R. Gombotz, Lexington; Michael S. Healy, E. Bridgewater; Larry R. Brown, Newton, all of Mass.

[73] Assignee: Enzytech, Inc., Cambridge, Mass.

[21] Appl. No.: 346,143

[22] Filed: May 1, 1989

[51] Int. Cl.$^5$ ............... A61K 9/58; B29B 9/00; C08K 7/16; B01J 13/02

[52] U.S. Cl. .................. 424/497; 264/9; 264/13; 264/14; 264/28; 424/489; 424/490; 424/499; 427/213.3; 427/213.36; 427/212; 428/402.24; 523/223

[58] Field of Search ............... 427/213.36, 213.3, 212, 427/213.31, 213.32; 428/402.24; 424/489, 501, 502, 499, 490, 497; 264/13, 9, 28, 14

[56] References Cited

U.S. PATENT DOCUMENTS

| | | | |
|---|---|---|---|
| 3,328,256 | 6/1967 | Gaunt | 424/501 |
| 3,373,232 | 3/1968 | Wise et al. | 264/13 |
| 3,523,906 | 8/1970 | Vrancken et al. | 264/4.6 |
| 3,523,907 | 8/1970 | Vrancken et al. | 264/4.6 |
| 3,646,177 | 2/1972 | Thompson et al. | 264/28 X |
| 3,655,838 | 4/1972 | Price et al. | 264/13 |
| 3,664,963 | 5/1972 | Pasin | 427/213.36 X |
| 3,689,607 | 9/1972 | Backlund | 264/28 X |
| 3,691,090 | 9/1972 | Kitajima et al. | 427/213.36 |
| 3,943,063 | 3/1976 | Morishita et al. | 427/213.36 |
| 3,960,757 | 6/1976 | Morishita et al. | 427/213.36 |
| 4,166,800 | 9/1979 | Fong | 427/213.36 |
| 4,272,398 | 6/1981 | Jaffe | 427/213.31 |
| 4,329,332 | 5/1982 | Couvreur | 424/501 X |
| 4,384,975 | 5/1983 | Fong | 427/213.36 |
| 4,389,330 | 6/1983 | Tice et al. | 427/213.36 |
| 4,675,189 | 6/1987 | Kent et al. | 424/490 |
| 4,713,249 | 12/1987 | Schröder | 427/213.3 X |
| 4,741,872 | 5/1988 | DeLuca et al. | 424/501 X |
| 4,818,542 | 4/1989 | DeLuca et al. | 427/213.3 X |
| 4,832,686 | 5/1989 | Anderson | 264/46 X |
| 4,873,102 | 10/1989 | Chang et al. | 264/13 X |
| 4,929,400 | 5/1990 | Rembaum et al. | 264/13 X |
| 4,981,625 | 1/1991 | Rhim et al. | 264/13 |

FOREIGN PATENT DOCUMENTS

| | | | |
|---|---|---|---|
| 081913 | 6/1983 | European Pat. Off. | 424/499 |
| 197776 | 10/1986 | European Pat. Off. | |
| 112321 | 7/1982 | Japan | |

OTHER PUBLICATIONS

Sefton, M. V., et al., 'Ethylene–Vinyl Acetate Copolymer Microsphere ...', *J. Pharm. Sci.*, vol. 73, No. 12 (1984), pp. 1859–61.

Sato, et al., Pharmaceutical Research, vol. 5, No. 1, 21–30 (1988).

*Primary Examiner*—Richard D. Lovering
*Assistant Examiner*—John M. Covert
*Attorney, Agent, or Firm*—Kilpatrick & Cody

[57] ABSTRACT

A process for preparing microspheres using very cold temperatures to freeze polymer-biologically active agent mixtures into polymeric microspheres with very high retention of biological activity and material. Polymer is dissolved in a solvent together with an active agent that can be either dissolved in the solvent or dispersed in the solvent in the form of microparticles. The polymer/active agent mixture is atomized into a vessel containing a liquid non-solvent, alone or frozen and overlayed with a liquified gas, at a temperature below the freezing point of the polymer/active agent solution. The cold liquified gas or liquid immediately freezes the polymer droplets. As the droplets and non-solvent for the polymer is warmed, the solvent in the droplets thaws and is extracted into the non-solvent, resulting in hardened microspheres.

18 Claims, 4 Drawing Sheets

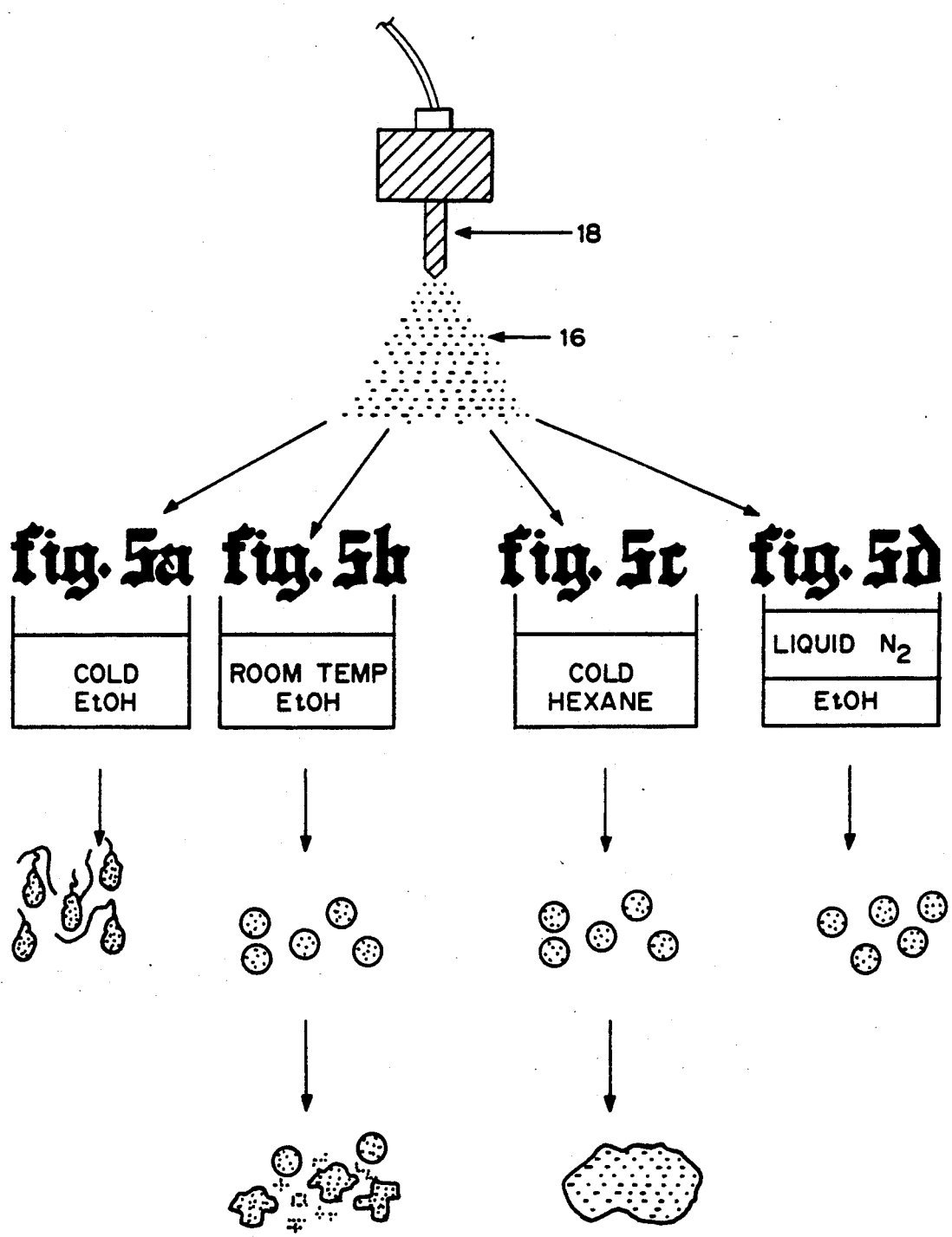

VERY LOW TEMPERATURE CASTING OF CONTROLLED RELEASE MICROSPHERES

BACKGROUND OF THE INVENTION

This invention generally relates to processes for making polymeric microspheres for controlled release of substances.

A variety of techniques are known by which active agents can be incorporated into polymeric microspheres. An example is spray drying. In spray drying, the polymer and active agent are mixed together in a solvent for the polymer, then the solvent is evaporated by spraying the solution, leaving polymeric droplets containing the active agent. Spray drying is reviewed in detail by K. Masters in "Spray Drying Handbook" (John Wiley & Sons, New York 1984); and Patrick B. Deasy in "Microencapsulation and Related Drug Processes" (Marcel Dekker, Inc., New York 1984). Spray drying works well for many agents but may inactivate some materials, particularly biologically active proteins, due to the heat generated during the process. In addition, considerable amounts of the material can be lost during the spray drying process due to sticking of the polymer to the large surface area on the sides of the chamber.

Solvent evaporation techniques have also been used to form microspheres. These techniques involve dissolving the polymer in an organic solvent which contains either dissolved or dispersed active agent. The polymer/active agent solution is then added to an agitated continuous phase which is usually aqueous and immiscible with the polymer/active agent. Emulsifiers can be included in the aqueous phase to stabilize the oil-in-water emulsion. The organic solvent is then evaporated over a period of several hours or more, thereby depositing the polymer around the core material. Solvent can be removed from the microspheres in a single step, as described in U.S. Pat. No. 3,737,337 and U.S. Pat. No. 3,523,906, or in U.S. Pat. No. 3,691,090 (under reduced pressure), or by the application of heat, as shown in U.S. Pat. No. 3,891,570. A two-step technique is described in U.S. Pat. No. 4,389,330. Freeze drying has also been used to remove the solvent from microspheres, as reported by Sato, et al, in "Porous Biodegradable Microspheres for Controlled Drug Delivery. I. Assessment of Processing Conditions and Solvent Removal Techniques," *Pharmaceutical Research* 5, 21-30 (1988).

Solvent evaporation works reasonably well for hydrophobic drugs but the amount of incorporated material is usually lower than the theoretical values due to loss of drug to the aqueous phase, as reported by Benita, et al., in "Characterization of Drug Loaded Poly(d,l-lactide) Microspheres," *J. Pharm. Sci.* 73, 1721-1724 (1984). If water soluble active agents are used, such as proteins, a much more significant loss of material can occur.

Phase separation techniques have also been used to form microspheres. These techniques involve the formation of a water-in-oil or an oil-in-water emulsion. The polymer is precipitated from the continuous phase onto the active agent by a change in temperature, pH, ionic strength or the addition of precipitants. For example, U.S. Pat. No. 4,675,189 describes the formation of poly(lactic-co-glycolic acid) microspheres containing hormonally active polypeptides. The polypeptide is first dissolved in the aqueous phase of a water-in-oil emulsion. Polymer is then precipitated around the aqueous droplets by addition of a non-solvent for the polymer such as silicon oil. The final product, as with most phase separation techniques, is in the form of a microcapsule. Microcapsules contain a core material surrounded by a polymer membrane capsule. The release kinetics of active agents from these devices can be difficult to control.

Although these phase separation techniques result in the formation of microspheres containing active agents, active agent is often lost during the solvent extraction process. In addition, as with spray drying, biologically active proteins may be denatured during the process.

Cold temperatures have also been employed in certain steps of the microsphere formation process. For example, U.S. Pat. No. 4,166,800 describes the use of temperatures between $-40°$ C. and $-100°$ C. along with a phase separation agent to stabilize the polymeric microspheres during phase separation.

A method using low temperature to form microspheres from an ethylene-vinyl acetate co-polymer, but not other polymers such as poly(lactic acid), is reported by Sefton, et al., in "Ethylene-Vinyl Acetate Copolymer Microspheres for Controlled Release of Macromolecules," *J. Pharm. Sci.* 73, 1859-1861 (1984). Polymer is dissolved in a dispersion of albumin in methylene chloride, added dropwise through a syringe into ethanol in a dry ice-ethanol bath ($-78°$ C.), where, upon hitting the cold ethanol, the drops gel and sink to the bottom of the container. After five to ten minutes the container is removed from the dry ice bath and allowed to warm to room temperature to extract the solvent from the microspheres. This system, however, does not work with other polymers such as poly(lactic acid).

Most of these methods result in the loss of some of the material being incorporated, and/or its activity. Many are very specific for a particular type of polymer, in part because the majority of these techniques rely on the use of a two phase system to form the microspheres, which are also very specific for each polymer type.

It is therefore an object of the present invention to provide a method for making microspheres containing biologically active materials with very little loss of activity and material.

It is a further object of the present invention to provide a method for making microspheres which can be used with a broad range of polymers.

It is a still further object of the present invention to provide such a process which is relatively quick, simple, and inexpensive.

SUMMARY OF THE INVENTION

A process for preparing microspheres using very cold temperatures to freeze polymer-biologically active agent mixtures into polymeric microspheres with very high retention of biological activity and material.

Polymer is dissolved in a solvent together with an active agent that can be either dissolved in the solvent or dispersed in the solvent in the form of microparticles. The polymer/active agent mixture is atomized into a vessel containing a liquid non-solvent, alone or frozen and overlayed with a liquified gas, at a temperature below the freezing point of the polymer/active agent solution. When the combination with the liquified gas is used, the atomized droplets freeze into microspheres upon contacting the cold liquified gas, then sink onto the frozen non-solvent layer. The frozen non-solvent is then thawed. As the non-solvent thaws, the microspheres which are still frozen sink into the liquid non-solvent. The solvent in the microspheres then thaws and is slowly extracted into the non-solvent, resulting in hardened microspheres containing active agent either as a homogeneous mixture of the polymer and the active agent or as a heterogeneous two phase system of discrete zones of polymer and active agent.

If a cold solvent is used alone, the atomized droplets freeze upon contacting the solvent, and sink to the bottom of the vessel. As the non-solvent for the polymer is warmed, the solvent in the microspheres thaws and is extracted into the non-solvent, resulting in hardened microspheres.

BRIEF DESCRIPTION OF THE DRAWINGS

FIG. 5 is a schematic comparing the microspheres produced by varying the process of FIG. 1: (a) using cold ethanol ($-78°$ C.) as the non-solvent without first freezing the polymer-agent solution; (b) using room temperature ethanol as the non-solvent without first freezing the polymer-agent solution; (c) using cold hexane as the non-solvent without first freezing the polymer-agent solution; and (d) using the method of FIG. 1.

DETAILED DESCRIPTION OF THE INVENTION

Microspheres made according to the method described below can be formed in a size suitable for injection through a 26-gauge needle (less than 50 micrometers in diameter) and can contain from less than 0.01% by weight up to approximately 50% by weight active agent. Active agents which can be incorporated into the microspheres include peptides, proteins, carbohydrates, polysaccharides, nucleic acids, lipids, steroids, and organic and inorganic drugs which are either hydrophobic or hydrophilic. Other excipients can also be entrapped in the microspheres, including, for example, dextran, poly(ethylene glycol), glucose and various salts.

Polymers that can be used to form the microspheres include bioerodible polymers such as poly(lactic acid), poly(lactic-co-glycolic acid), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate copolymers and other acyl substituted cellulose acetates and derivatives thereof, non-erodible polyurethanes, polystyrenes, polyvinyl chloride, polyvinyl fluoride, poly(vinyl imidazole), chlorosulphonated polyolefins, and polyethylene oxide. Almost any type of polymer can be used provided the appropriate solvent and non-solvent are found which have the desired melting points. In general, a polymer solution is prepared containing between 1% polymer and 20% polymer, preferably 5–10% polymer.

There are two principal embodiments of the system for making microspheres: a combination cold liquified gas—frozen non-solvent system and a cold non-solvent system, wherein "cold" is defined as a temperature which will immediately freeze the polymer and "non-solvent" is a liquid in which the polymer is not soluble.

Figure 1:
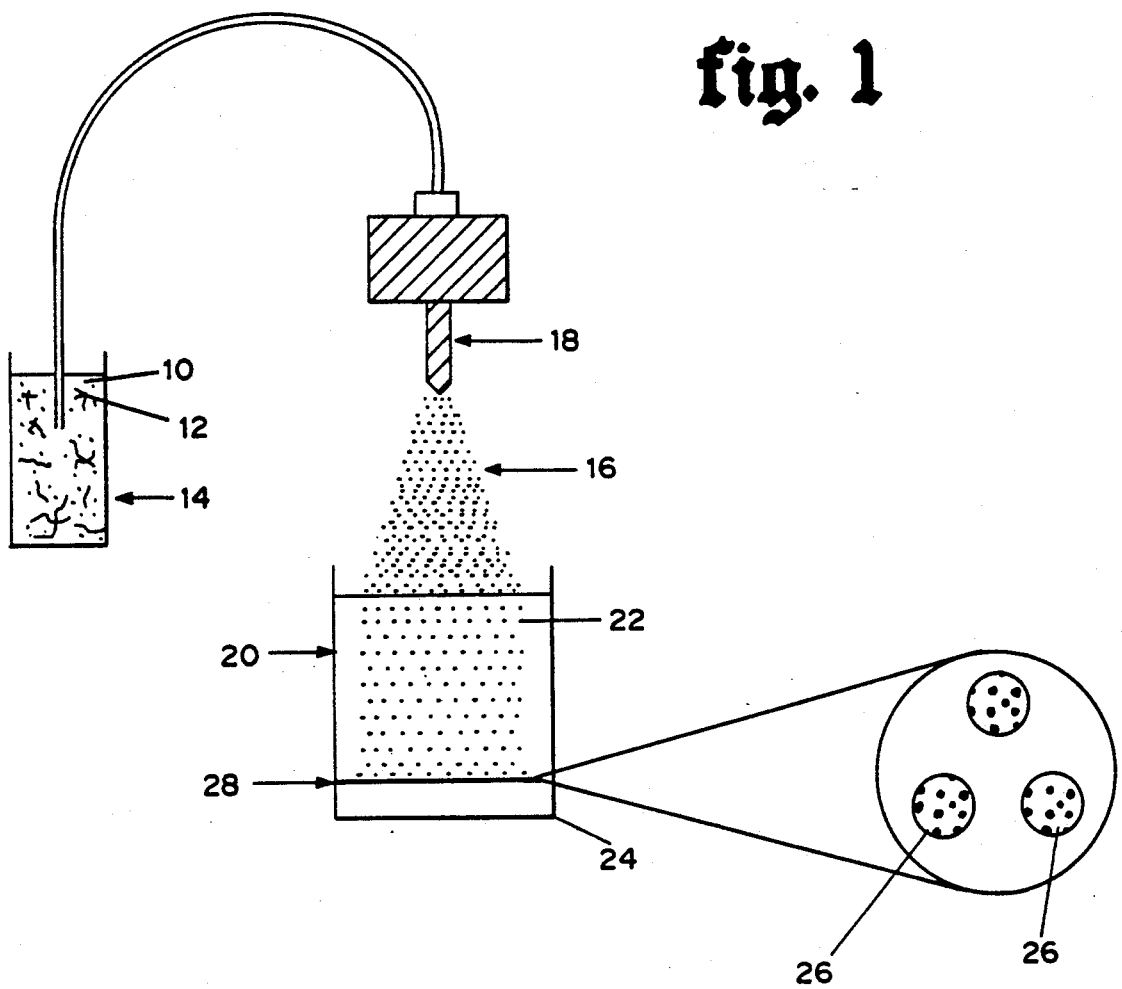
FIG. 1 is a schematic of the process of the present invention for making microspheres containing an agent to be incorporated using a liquified gas, frozen non-solvent system.
Figure 2A:
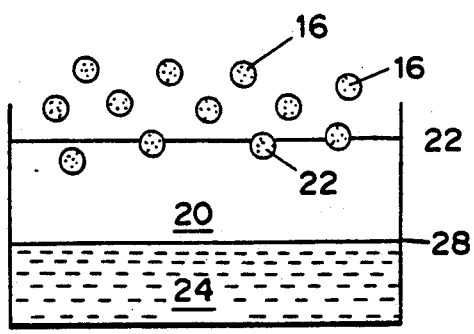
FIG. 2 a schematic of the freezing and solvent extraction steps of FIG. 1 in detail.
Figure 2B:
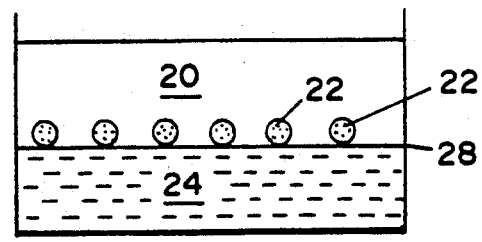
Figure 2C:
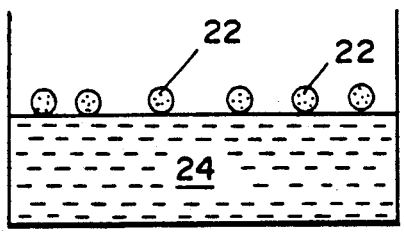
Figure 2D:
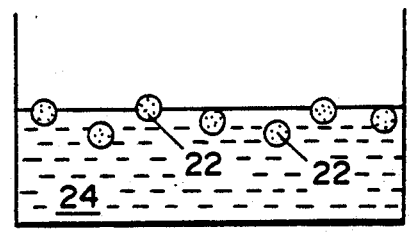
Figure 2E:
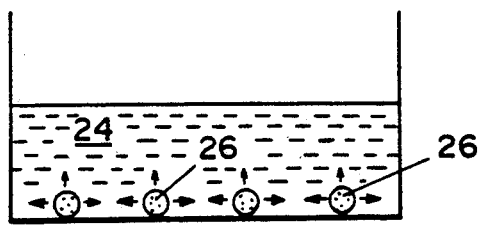
Figure 2F:
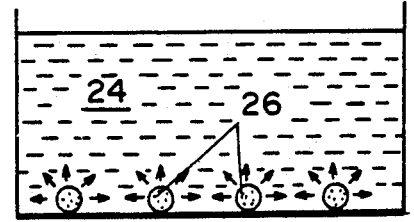

The process is shown schematically in FIG. 1 for a liquified gas-frozen solvent system. Polymer 10 and agent to be incorporated 12 in solution 14 are atomized 16 using an ultrasonic device 18 into a cold liquified gas 20. The microspheres 22 are immediately frozen by the liquified gas 20. The non-solvent 24 thaws and the frozen spheres 22 sink into the very cold non-solvent 24. The non-solvent 24 extracts the solvent 14 from the spheres 22 as they thaw, leaving microspheres 26 containing the incorporated agent.

The liquified gas 20 can be liquid argon ($-185.6°$ C.), liquid nitrogen ($-195.8°$ C.), liquid oxygen ($-182.9°$ C.) or any other gas that results in the immediate freezing of the atomized droplets into frozen spheres 22.

Alternatively, a cold non-solvent for the polymer can be substituted for the combination of liquified gas-frozen non-solvent, provided the temperature of the non-solvent is below the freezing temperature of the polymer/active agent solution.

In both embodiments, it is important that the solution or suspension of polymer and active agent freeze immediately upon contacting the cold liquid, and then be slowly thawed and the polymer solvent extracted from the microspheres, leaving behind the polymer and active agent.

FIG. 2 is a schematic of the freezing and solvent extraction steps of the process depicted in FIG. 1. In FIG. 2a, the atomized droplets 16 freeze when they contact the liquified gas 20 (liquid nitrogen), forming frozen spheres 22. In FIG. 2b, these sink to the surface 28 of the frozen non-solvent (ethanol) 24. In FIG. 2c, the liquid gas 20 is evaporated and, in FIG. 2d, the spheres 22 begin to sink into the non-solvent 24 as the non-solvent thaws. In FIG. 2e, the solvent 14 in the spheres 22 is extracted into the non-solvent 24 to form microspheres 26 containing the polymer and the active agent. In FIG. 2f, other non-solvents such as hexane are added to the non-solvent (ethanol) to increase the rate of solvent extraction from certain polymers, where appropriate, for example, when spheres are formed of poly(lactic-co-glycolic acid) polymers.

The thawing rate is dependent on the choice of solvents and non-solvents, and the ambient temperature at which the system is thawed. It is important to select a solvent for the polymer having a higher melting point than the non-solvent for the polymer so that the non-solvent melts first, allowing the frozen microspheres to sink into the liquid where they later thaw. If a cold liquid non-solvent system for making the polymeric microspheres is used, the microspheres will sink immediately into the non-solvent. As the solvent in the microsphere thaws, it is extracted into the non-solvent. The solvent for the polymer and the non-solvent for the polymer must be miscible to allow extraction of the solvent from the microspheres. Table 1 shows some exemplary polymer/solvent/non-solvent systems that can be used in this process along with their melting points.

An advantage of this method is that surface active agents are not required in most cases, as in most processes for making microspheres involving formation of an emulsion, as in phase separation. There are many drug delivery applications where surface active agents, or emulsifiers, interfere with release or cause an undesirable reaction. However, when desired, other materials can be incorporated into the microspheres with the biologically active agents. Examples of these materials are salts, metals, sugars, surface active agents, acids, bases, stabilizers, and release enhancing agents. Surface active agents may also be added to the non-solvent during extraction of the solvent to reduce the possibility of aggregation of the microspheres.

TABLE 1

Polymers and Appropriate Solvents and Non-Solvents Systems, with Solvent and Non-Solvent Melting Points

| POLYMER | SOLVENT | NON-SOLVENT |
| --- | --- | --- |
| Poly(lactic acid) | Methylene Chloride (−95.1) | Ethanol (−114.5) |
|  | Chloroform (−63.5) | Methanol (−97.5) |
| Poly(lactic-co-glycolic acid) | Ethyl Acetate (−83.6) | Ethanol (−114.5) |
|  | Acetone (−95.4) | Ethyl ether (−116.3) |
|  | Methylene Chloride (−95.1) | Pentane (−130) Isopentane (−160) |
| Poly(caprolactone) | Methylene Chloride (−95.1) | Ethanol (−114.5) |
| Poly (vinyl alcohol) | Water (0) | Acetone (−95.4) |
| Ethylene-vinyl acetate | Methylene Chloride (−95.1) | Ethanol (−114.5) |

The polymer/active agent/solvent mixture can be sprayed into the cold liquid, either the liquified gas or the cold non-solvent, using a variety of devices which can be used to form small droplets, including sonic nozzles, pressure nozzles, pneumatic nozzles and rotary atomizers.

A wide range of sizes of microspheres can be made by varying the droplet size, for example, by changing the nozzle diameter. If very large spheres are desired, the spheres can be extruded through a syringe directly into the cold liquid. Increasing the inherent viscosity of the polymer solution can also result in an increasing microspheres size. The size of the spheres produced by this process can range from greater than 1000 down to 5 micrometers in diameter. A preferred size range for injectable microspheres is from 30 to 50 micrometers in diameter. The microspheres made by this technique are spherical in shape, without irregularities.

The microspheres made by this process can be either homogeneous or heterogeneous mixtures of the polymer and the active agent. Homogeneous mixtures are produced when the active agent and the polymer are both soluble in the solvent, as in the case of certain hydrophobic drugs such as steroids. Heterogeneous two phase systems having discrete zones of polymer and active agent are produced when the active agent is not soluble in the polymer/solvent, and is introduced as a suspension in the polymer/solvent solution, as with hydrophilic compounds such as proteins in methylene chloride.

The present invention is further described by the following non-limiting examples which demonstrate that the process is applicable to a wide range of polymers, solvents, and substances to be incorporated within the microspheres.

EXAMPLE 1

Preparation of poly(L-lactic acid) microspheres containing SOD 0.7 g of poly(L-lactic acid) (Polysciences, Inc., Warrington, Pa., mw 2000) was dissolved in 14.0 ml of methylene chloride to produce a 5% (w/v) polymer solution. 3.36 ml of this polymer solution was added to 42 mg of the enzyme superoxide dismutase (SOD) (American International Chemicals, Inc., Natick, Mass.), to yield a 20% by weight superoxide dismutase (SOD) in 5% polymer solution. Similar preparations were made containing 10% and 5% SOD. The mixture was sonicated using a VirSonic 300 Ultrasonic Probe, Virtis Company, Inc., Gardiner, N.Y., to decrease the size of the protein particles, using the method of copending U.S. Ser. No. 07/345,684 entitled "Process for Producing Small Particles of Biologically Active Molecules" filed May 1, 1989 by Wayne R. Gombotz, Michael S. Healy, Larry R. Brown, and Henry E. Auer, and then placed in a 5 ml gas tight syringe. A 150 ml amount of 100% ethanol was added to a 8×6×1.5 in poly(propylene) tray. To this was added 300 ml of liquid nitrogen (−195.8° C.) which resulted in a frozen layer of ethanol covered by a layer of liquid nitrogen. The polymer/protein mixture was extruded from the syringe via a syringe pump at a rate of 6.75 ml/min, into an ultrasonic nozzle (Model 8700-60MS Microspray Atomic Nozzle, SonoTek Corp., Poughkeepsie, N.Y.) that was placed over the liquid nitrogen/frozen ethanol solution. The nozzle atomized the mixture into droplets which froze upon contacting the liquid nitrogen and formed microspheres which then sank onto the frozen ethanol.

Figure 3:
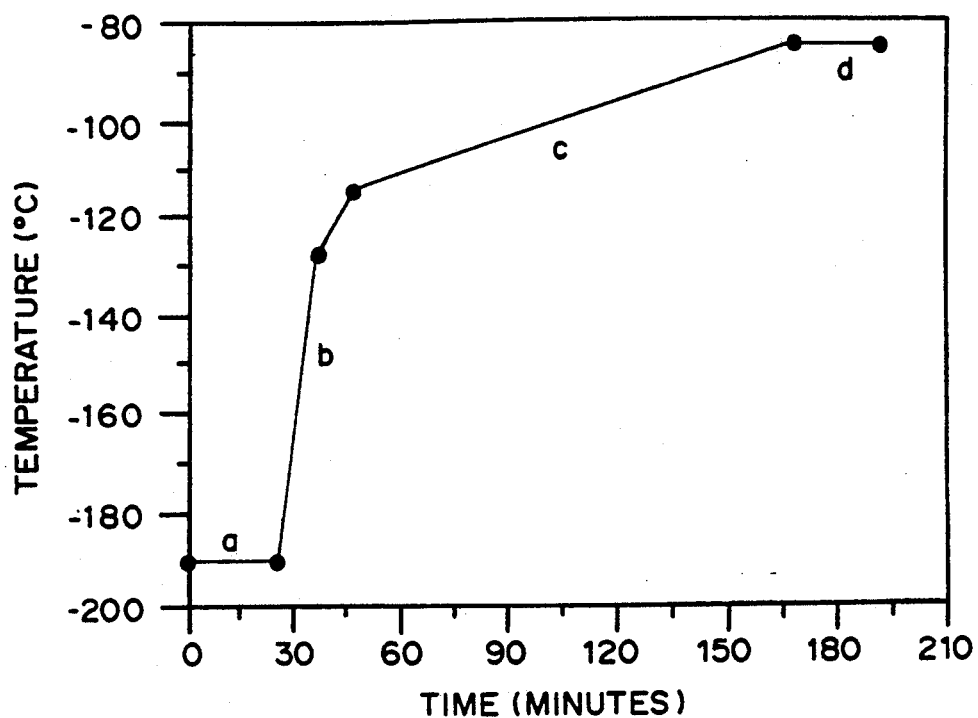
FIG. 3 is a graph of temperature of the ethanol in the process of the present invention as described in example 1 versus time in minutes: (a) as the liquified nitrogen is evaporated; (b) as the ethanol melts; (c) as the ethanol warms and the solvent in the microspheres begins to melt; and (d) as the temperature of the ethanol and microspheres begins to stabilize.

The container was placed in a −80° C. freezer where the liquid nitrogen evaporated and the ethanol slowly melted over time. FIG. 3 is a graph of the temperature of the ethanol over time. At (a), the ethanol is still frozen. At (b), the microspheres are beginning to sink into the ethanol as it melts. Once the temperature reaches −95.1° C., the methylene chloride is extracted from the polymer/protein spheres into the ethanol (c and d). After three days the container was removed from the freezer and the microspheres were filtered from the solvent. They were then dried in a vacuum desiccator for 24 hrs.

Under light microscopy, the microspheres were round and had diameters ranging from 30 to 50 micrometers. Scanning electron microscopy of microsphere cross sections showed the spheres to be porous.

Figure 4:
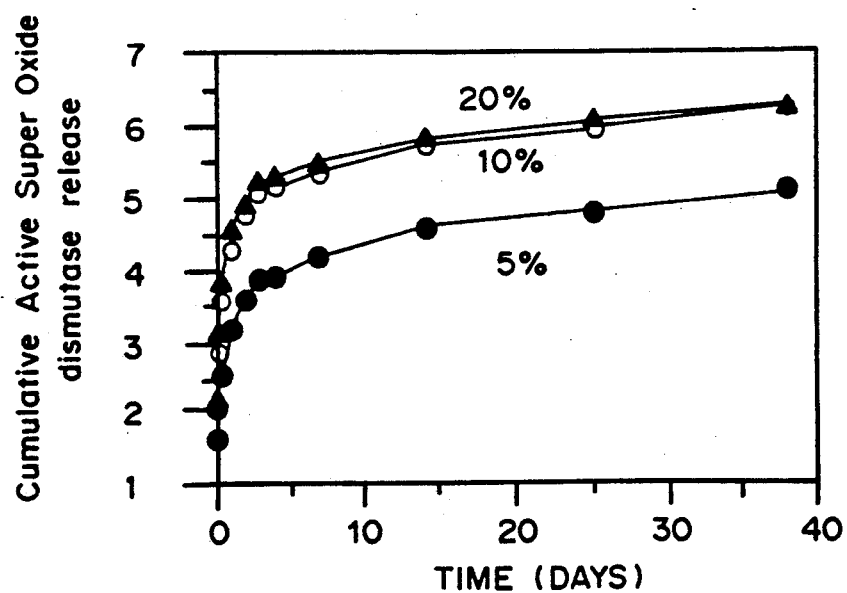
FIG. 4 is a graph of the release of active superoxide dismutase (SOD) from poly(L-lactide) microspheres ($\mu g$ SOD released/mg SOD loaded microspheres) over time (days) at three loadings: 5% SOD, 10% SOD, and 20% SOD.

The dried microspheres were suspended in a phosphate buffered solution, pH 7.4, and the release of the superoxide dismutase was monitored. Active protein was released over a time period of 38 days, as shown in FIG. 4. The specific activity of the SOD released was 90% of the starting specific activity. Release was compared for three different loadings: 5%, 10% and 20%. The 5% loaded microspheres released the least amount of enzyme, with a greater amount being released from the 10% and 20% loaded microspheres, approximately 5-6 micrograms SOD/mg of microsphere for both loadings.

The microspheres containing 20% SOD (60 mg) were suspended in a 1.5 ml aqueous solution containing 5.5 mg of carboxymethylcellulose, 75 mg of D-mannitol and 1.5 mg of polysorbate 80. The microspheres were then injected into a rat through a 26-gauge needle at a concentration of 40 mg/ml. No clogging of the needle occurred demonstrating that these microspheres can be used for injection through a narrow gauge needle.

EXAMPLE 2

Preparation of poly(DL-lactide-co-glycolide) (50:50) microspheres containing SOD The procedure in Example 1 was repeated using poly(DL-lactide-co-glycolide) (50:50) Resomer L-104, (Boehringer Ingelheim, W.Germany) to form the microspheres. After the microspheres were extracted for three days in the cold ethanol at −80° C., 100 ml of hexane was added and the extraction was continued for another 24 hrs. The microspheres were then filtered and dried in a vacuum desiccator. Results of the size analysis and SEM observations were similar to those in example 1.

EXAMPLE 3

Preparation of Poly(DL-lactide-co-glycolide) (50:50) microspheres containing HRP The procedure of example 1 was repeated using Poly(DL-lactide-co-glycolide) (50:50) in methylene chloride to form microspheres containing horse radish peroxidase (HRP) (Sigma Chemical Co.) extracted into ethanol and hexane. Results were similar to those in Example 1.

EXAMPLE 4

Preparation of Poly(L-lactic acid) 2000 microspheres containing mitomycin C

Poly(L-lactic acid) 2000 in methylene chloride with 5% by weight mitomycin C was sprayed into ethanol. Mitomycin C is a 334 dalton chemotherapeutic agent. Results of the size analysis and SEM were similar to those in example 1. This example demonstrates that molecules other than proteins can be incorporated into the microspheres.

EXAMPLE 5

Preparation of Poly(L-lactic acid) 2000 microspheres containing etoposide

Etoposide is an antineoplastic agent that is soluble in organic solvents. Poly(L-lactic acid) 2000 was dissolved in methylene chloride with 40% by weight etoposide and sprayed into ethanol. The resulting microspheres were 30 to 50 micrometer in diameter. Continuous release of etoposide was measured over a one week period. The results demonstrate that microspheres can be made from solutions containing both dissolved polymer and dissolved active agent.

EXAMPLE 6

Preparation of microspheres from a blend of poly(L-lactic acid) and poly(DL-lactic-co-glycolic acid) containing hemoglobin A (1:1) blend of 5% poly(L-lactic acid) and 5% poly(DL-lactic-co-glycolic acid) with bovine hemoglobin (Sigma Chemica Co.) suspended in methylene chloride was sprayed into ethyl ether. Results of size analysis and SEM were similar to those in example 1, demonstrating that the process is applicable to microspheres formed from polymer blends. Release of the hemoglobin from the microsphere into physiological buffer was achieved over a two month period.

EXAMPLE 7

Preparation of microspheres from Poly(L-lactic acid) 2000 containing hemoglobin using liquid Argon Hemoglobin suspended in a solution of poly(L-lactic acid) 2000 in methylene chloride was sprayed into liquid argon and frozen ethanol. Under the light microscope, the resulting dried spheres were seen to contain a heterogeneous dispersion of small hemoglobin particles distributed throughout the polymer matrix. This example demonstrates the applicability of other gases in the process.

Examples 8 through 12 describe the preparation of microspheres from different polymer solutions, demonstrating the variety of different polymers, solvents and non-solvents that can be used in the process of the present invention.

EXAMPLE 8

Preparation of polyvinyl alcohol microspheres

A 5% by weight solution of polyvinyl alcohol (Elvanol, du Pont de Nemour & Co., Wilmington, Del.) was dissolved in water. This was atomized through an ultrasonic nozzle into liquid nitrogen covering a layer of frozen acetone. After thawing for three days the 30 to 50 micrometer diameter microspheres were filtered and dried.

EXAMPLE 9

Preparation of Poly(caprolactone) microspheres

A 5% by weight solution of poly(caprolactone) (Sigma Chemical Co.) was dissolved in methylene chloride. This was atomized through an ultrasonic nozzle into liquid nitrogen covering a layer of frozen ethanol. After thawing for three days the microspheres were filtered and dried.

EXAMPLE 10

Preparation of ethylene vinyl acetate copolymer microspheres

A 5% by weight solution of ethylene-vinyl acetate copolymer (Vynathene, USI Chemicals, Cincinnati, Ohio) was dissolved in methylene chloride. This was atomized through an ultrasonic nozzle into liquid nitrogen covering a layer of frozen ethanol. After thawing for three days the microspheres were filtered and dried.

EXAMPLE 11

Preparation of poly(lactic acid) 2000 microspheres in a cold liquid solvent

A 5% by weight solution of poly(l-lactic acid) was dissolved in methylene chloride. This was atomized through an ultrasonic nozzle into cold isopentane (−141.2° C.). The droplets froze into spheres upon contact with the cold liquid and sank to the bottom of the container. The microspheres were placed in an −80° C. freezer for three days to extract the solvent. They were then filtered and dried. This example illustrates that a cold non-solvent for the polymer can be used, if its temperature is below the melting point of the polymer/solvent solution.

EXAMPLE 12

Demonstration of Criticality of the temperature

Experiments were conducted to determine the necessity of using a liquid that has a temperature below the freezing point of the polymer/solvent solution. A 5% solution of poly(L-lactic acid) was prepared in methylene chloride. This solution was atomized into six different systems (a) cold ethanol (−80° C.); (b) room temperature ethanol (23° C.); (c) cold hexane (−80° C.); (d) liquid nitrogen layered over frozen ethanol (−195.8° C.); (e) room temperature hexane (23° C.); and (f) cold isopentane (−80° C.). The results of systems (a) through (e) are shown in FIG. 5. (In (a), atomized droplets of polymer were sprayed into cold ethanol (−80° C.). Only teardrop shaped polymer particles and polymer fibers were produced. In (b), atomized polymer droplets were sprayed onto room temperature ethanol. Although spheres formed initially, these spheres gradually took on amorphous shapes and some of them fused. In (c), atomized droplets were sprayed onto cold hexane (−80° C.). Room temperature hexane was also used (e). In both cases, although spheres formed initially, these fused to form a polymer film. Similar results were obtained spraying into isopentane (−80° C.) (f).

In (d), the atomized droplets were sprayed into liquid nitrogen layered over frozen ethanol and spherical, non-aggregated microspheres were formed. As described in example 11, well shaped microspheres were also formed when the isopentane was at a temperature of −141.2° C. In both embodiments of the system, the liquified gas overlaying a frozen non-solvent and the cold temperature solvent, the atomized polymer droplets were frozen upon hitting the solvent. Temperatures warmer than those which resulted in the immediate freezing of the polymer were not effective in producing uniformly spherical non-aggregated polymeric microspheres.

Modifications and variations of the present invention, a method for making microspheres, and products thereof, will be obvious to those skilled in the art from the foregoing detailed description of the invention. Such modifications and variations are intended to come within the scope of the appended claims.

We claim:

1. A method for preparing polymeric microspheres comprising
   a) freezing droplets of polymer solution by atomizing the droplets into a liquified gas, having a temperature below the freezing point of the polymer solution effective to immediately freeze the atomized polymer solution upon contact, said liquified gas overlaying a layer of frozen liquid non-solvent for the polymer, wherein the polymer solvent is miscible in the liquid non-solvent;
   b) thawing the polymer solvent in the frozen droplets of polymer solution; and
   c) extracting the solvent from the droplets into a liquid non-solvent to form spherical polymeric microspheres.

2. The method of claim 1 further comprising:
   evaporating the liquified gas after freezing the droplets of polymer solution; and
   thawing the frozen liquid non-solvent to extract the solvent from the frozen droplets.

3. The method of claim 1 wherein the freezing non-solvent and the extracting non-solvent are the same.

4. The method of claim 1 further comprising providing a biologically active agent to be incorporated in the microspheres selected from the group consisting of proteins, short chain peptides, polysaccharides, nucleic acids, lipids, steroids, and organic and inorganic drugs.

5. The method of claim 1 wherein the liquified gas is selected from the group consisting of liquid argon (−185.6° C.), liquid nitrogen (−195.8° C.), and liquid oxygen (−182.9° C.).

6. The method of claim 1 wherein the polymer is selected from the group consisting of poly(lactic acid), poly(lactic-co-glycolic acid), poly(caprolactone), polycarbonates, polyamides, polyanhydrides, polyamino acids, polyortho esters, polyacetals, polycyanoacrylates, polyurethanes, polyacrylates, ethylene-vinyl acetate and other acyl substituted cellulose acetates and derivatives thereof, polystyrenes, polyvinyl chloride, polyvinyl fluoride, poly(vinyl imidazole), chlorosulphonated polyolefins, polyethylene oxide, and copolymers and blends thereof.

7. The method of claim 1 further comprising removing the microspheres from the non-solvent.

8. The method of claim 1 wherein the polymer solution has a concentration between 1% and 20%.

9. The method of claim 1 wherein the microsphere has a final concentration of up to 50% by weight active non-polymeric components.

10. A porous polymeric microsphere having a diameter between 5 and 1000 microns, spherical in shape, not containing water in the polymer, formed by
    a) freezing droplets of polymer solution by atomizing the droplets into a liquified gas, having a temperature below the freezing point of the polymer solution effective to immediately freeze the atomized polymer solution upon contact, said liquified gas overlaying a layer of frozen liquid non-solvent for the polymer, wherein the polymer solvent is miscible in the liquid non-solvent;
    b) thawing the polymer solvent in the frozen polymeric droplets; and
    c) extracting the solvent from the polymeric droplets into a liquid non-solvent to form spherical polymeric microspheres.

11. The microspheres of claim 10 wherein the polymer is selected from the group consisting of poly(lactic acid), poly(lactic-co-glycolic acid), poly(caprolactone), polycarbonates, polyamides, polyanhydrides, polyamino acids, polyortho esters, polyacetals, polycyanoacrylates, polyurethanes, polyacrylates, ethylene-vinyl acetate and other acyl substituted cellulose acetates and derivatives thereof, polystyrenes, polyvinyl chloride, polyvinyl fluoride, poly(vinyl imidazole), chlorosulphonated polyolefins, polyethylene oxide, and copolymers and blends thereof.

12. The microspheres of claim 10 further comprising a biologically active agent incorporated in the microspheres selected from the group consisting of proteins, short chain peptides, polysaccharides, nucleic acids, lipids, steroids, and organic and inorganic drugs, having greater than 90% of the biological activity of the agent before incorporation in the microspheres.

13. The microspheres of claim 12 further comprising a material selected from the group consisting of salts, metals, sugars, surface active agents, acids, bases, stabilizers, and release enhancing agents.

14. The microspheres of claim 12 wherein the polymer and agent form a heterogeneous mixture.

15. The microspheres of claim 12 wherein the polymer and agent form a homogeneous mixture.

16. The microspheres of claim 12 comprising a biologically active agent, wherein the agent after incorporation maintains greater than 90% of the biological activity present prior to incorporation into the microspheres, and said microspheres do not contain surface active agents.

17. The microspheres of claim 12 wherein the microsphere has a final concentration of up to 50% by weight non-polymeric components.

18. The microspheres of claim 12 wherein the microspheres have diameters of approximately 50 microns or less.

* * * * *